United States Patent
Yang et al.

(10) Patent No.: US 8,633,332 B2
(45) Date of Patent: Jan. 21, 2014

(54) EFFICIENT ISOLATION OF CIMIRACEMATE A, AND METHODS OF USE

(75) Inventors: Lai Hung Cindy Yang, Hong Kong (CN); Allan Sy Lau, Hong Kong (CN)

(73) Assignees: Purapharm Company Limited, Hong Kong (CN); Versitech Limited, Hong Kong (CN)

( * ) Notice: Subject to any disclaimer, the term of this patent is extended or adjusted under 35 U.S.C. 154(b) by 46 days.

(21) Appl. No.: 13/379,008

(22) PCT Filed: Jun. 21, 2010

(86) PCT No.: PCT/IB2010/001772
§ 371 (c)(1),
(2), (4) Date: Apr. 9, 2012

(87) PCT Pub. No.: WO2010/150102
PCT Pub. Date: Dec. 29, 2010

(65) Prior Publication Data
US 2012/0190882 A1    Jul. 26, 2012

Related U.S. Application Data

(60) Provisional application No. 61/218,962, filed on Jun. 21, 2009.

(51) Int. Cl.
*C07C 69/76* (2006.01)
(52) U.S. Cl.
USPC .......................................................... 560/61
(58) Field of Classification Search
USPC ...................................... 560/1, 8, 51, 55, 61
See application file for complete search history.

(56) References Cited

FOREIGN PATENT DOCUMENTS

WO   WO 2008/069604   *   6/2008
WO   WO 2010/079406        7/2010

OTHER PUBLICATIONS

Burdette et al. (Black Cohosh (*Cimicifuga racemosa* L.) Protects against Menadione-Induced DNA Damage through Scavenging of Reactive Oxygen Species: Bioassay-Directed Isolation and Characterization of Active Principles, J. Agric. Food Chem., 50, 7022-7028, published on Web Oct. 23, 2002).*

Chen et al. (Cimiracemates A-D, phenylpropanoid esters from the rhizomes of *Cimicifuga racemosa*, Phytochemistry, vol. 61, 409-413 (2002).*

Tian et al. (*Cimicifuga foetida* extract inhibits proliferation of hepatocellular cells via induction of cell cycle arrest and apoptosis, Journal of Ethnopharmacology, vol. 114, pp. 227-233, 2007).*

Burdette, J. E., et al., "Black Cohosh (*Cimicifuga racemosa* L.) Protects against Menadione-Induced DNA Damage through Scavenging of Reactive Oxygen Species: Bioassay-Directed Isolation and Characterization of Active Principles," *Journal of Agricultural and Food Chemistry*, Oct. 2002, vol. 50, pp. 7022-7028.

Chen, S.-N., et al., "Cimiracemates A-D, phenylpropanoid esters from the rhizomes of *Cimicifuga racemosa*," Phytochemistry, Apr. 2002, vol. 61, pp. 409-413.

He, K. et al., "*Cimicifuga* species identification by high performance liquid chromatography-photodiode array/mass spectrometric/evaporative light scattering detection for quality control of black cohosh products," *Journal of Chromatography A*, Mar. 2006, vol. 1112, pp. 241-254.

Huie, C. W., "A review of modern sample-preparation techniques for the extraction and analysis of medicinal plants," *Anal Bioanal Chem*, Apr. 2002, vol. 373, pp. 23-30.

Li, W. et al., "High-performance liquid chromatographic analysis of Black Cohosh (*Cimicifuga racemosa*) constituents with in-line evaporative light scattering and photodiode array detection," *Analytica Chinica Acta*, Aug. 2002, vol. 471, pp. 61-75.

Stromeier, S. et al, "Phenolic Esters from the Rhizomes of *Cimicifuga racemosa* do no Cause Proliferation Effects in MCF-7 Cells," *Planta Med*, Jun. 2005, vol. 71, pp. 495-500.

Yang et al., Identification of the Bioactive Constituent and Its Mechanisms of Action in Mediating the Anti-Inflammatory Effects of Black Cohosh and Related *Cimicifuga* species on Human Primary Blood Macrophages, May 11, 2009, Vo. 52, No. 21, Journal of Medicinal Chemistry.

* cited by examiner

*Primary Examiner* — Wu-Cheng Winston Shen
*Assistant Examiner* — Blaine G Doletski
(74) *Attorney, Agent, or Firm* — Saliwanchik, Lloyd & Eisenschenk

(57) ABSTRACT

A method for isolating cimiracemate A from a *Cimicifuga* species is disclosed, comprising the steps of a) providing a sufficient quantity of raw materials from the *Cimicifuga* species, b) mixing the raw materials from the *Cimicifuga* species with an aqueous polar solvent at a temperature of about 20° C. to about 28° C. to obtain a solvent extract comprising cimiracemate A, and c) isolating cimiracemate A from the solvent extract.

21 Claims, 9 Drawing Sheets

EFFICIENT ISOLATION OF CIMIRACEMATE A, AND METHODS OF USE

CROSS REFERENCE TO A RELATED APPLICATION

This application is a National Stage Application of International Application Number PCT/AB2010/001772, filed Jun. 21, 2010; which claims priority to U.S. Provisional Application No. 61/218,962, filed Jun. 21, 2009; all of which are hereby incorporated by reference in their entirety.

BACKGROUND OF THE INVENTION

Various species of *Cimicifuga* have been used as therapeutics for inflammatory conditions in Chinese, Korean, and Japanese medicine. Similarly, compositions containing black cohosh, known botanically as *Cimicifuga racemosa* L. Nutt (also *Actaea racemosa*), are widely used as herbal dietary supplements in the United States and Europe. Historically, Native American women used black cohosh for the treatment of malaise, malaria, rheumatism, abnormal kidney function, sore throat, menstrual irregularities, and diseases associated with childbirth (Blementhal et al., 2000). In Asian countries, this herb and other species of *Cimicifuga* including *Cimicifuga dahurica* (Turcz.) Maxim., *Cimicifuga foetida* L., and *Cimicifuga heracleifolia* Kom. are used to treat inflammation, fever, headache, pain, sore throat, and chills (Foster, 1999; Kusano, 2001; Kim et al., 2004). However, the underlying mechanisms of action for these herbs remain to be fully elucidated.

The biological activities of black cohosh have been investigated previously. In vivo, it was demonstrated that black cohosh extracts inhibit the anti-IgE-induced passive cutaneous anaphylaxis reaction in Sprague-Dawley rats in a dose-dependent manner (Kim et al., 2004). In vitro, the herbal extracts inhibit the transcription of cytokines including IL-4, IL-5 and TNF-$\alpha$ by inflammatory agents such as PMA and A2387 in HMC-1 human leukemia mast cells (Kim et al., 2004). Other studies also demonstrated the inhibitory effects of black cohosh extract on histamine, bradykinin and COX-2 mediated inflammatory actions (Kim and Kim, 2000). However, the active components present in the extract are unknown.

Cimiracemate A is the ester formed between isoferulic acid and 3-(30,40-dihydroxylphenyl)-2-keto-propanol (Chen et al., 2005). Cimiracemate A is a naturally occurring compound possessing a 1,7-diaryl skeleton. Other compounds with this 1,7-diaryl skeleton have significant biological activities (Roughley & Whiting, 1973). For instance, curcumin, a natural pigment isolated from *Curcuma longa* has been reported to inhibit growth of several types of malignant cells (Chen et al., 1999; Aggarwal et al., 2004) and especially in the case of HIV infection (Vlietinck et al., 1998). Yakuchinone B extracted from the seeds of *Alpina oxyphylla* (Itokawa et al., 1982) is active against hypercholesterolemia and atherosclerosis (Ohishi et al., 2001).

Cimiracemate A has been found to suppress LPS-induced TNF-$\alpha$ in human macrophages and to inhibit LPS-induced MAP kinase activities as well as activation of specific transcription factors. Furthermore, cimiracemate A may have additional health benefits including reactive oxygen species scavengers (Burdette et al., 2002). Taken together, compounds, like cimiracemate A, with the 1,7-diaryl skeleton may have multiple bioactivities that can act via multiple cell-dependent mechanisms.

*C. racemosa* has been experiencing a dramatic increase in consumption in the United States and Europe. Its products are prepared in the form of isopropanolic and ethanolic extracts currently available to consumers in a range of formulations and dosages. The use of this herb has been based on extracts rather than the individual bioactive components. Although some compounds have been isolated from *C. racemosa*, including triterpene glycosides and phenolics, their bioactivities and consistent presence in the extracts remain to be determined (Kennelly et al., 2002).

Another isolated *C. racemosa* component is 23-epi-26-deoxyactein. The 23-epi-26-deoxyactein component is currently used as the chemical marker to standardize commercial *C. racemosa* products. The rationale for its usage is its abundance in the extract (Pepping, 1999). Thus, the chemical marker used for the standardization of *C. racemosa* extracts is not necessarily representative of the bioactivity of this herb.

Many different species of *cimicifuga* are traditionally used to cure inflammation; however, as indicated in FIG. 10, their chemical constituents are relatively different under the same analyzing condition. Although different methods have been developed to distinguish *Cimicifuga* species using fingerprinting approach (He et al., 2006; Li et al., 2002), the complexity and the variation of the chemical constituents of the herbs limit their use in species identification.

Therefore, a great need exists for the extraction and isolation of cimiracemate A for subsequent use as a therapeutic agent. In addition, there is a need for a bioactive marker that can be used to identify the members of the *Cimicifuga* genus, for example: *C. racemosa*, *C. dahurica* (Turcz.) Maxim., *C. foetida* L., and *C. heracleifolia* Kom. Ideally the bioactive marker could can also be used to standardize extracts of *Cimicifuga* species for use as anti-inflammatory agents for the treatment of inflammatory-associated diseases and to distinguish species based on the chemical profile of each sample.

BRIEF SUMMARY

The subject invention provides materials and methods for isolating and extracting cimiracemate A from *Cimicifuga*. In accordance with the subject invention, the isolated cimiracemate A can be used as a therapeutic composition and/or as a dietary supplement. In addition, the isolated cimiracemate A can be used as a bioactive chemical marker and standard for various species of *Cimicifuga*.

In a preferred embodiment the subject invention provides a method for purifying cimiracemate A, comprising the steps of:
 a) providing a sufficient quantity of material of a *Cimicifuga* species;
 b) grinding the raw material;
 c) mixing the ground material with an aqueous solvent; and
 d) isolating cimiracemate A.

Advantageously, the subject invention provides higher and more consistent yields of isolated cimiracemate A from *Cimicifuga* species. The novel isolation procedure of the subject invention is also more rapid and convenient.

The subject invention provides isolated cimiracemate A for treatment of, for example, malaise, malaria, rheumatism, abnormal kidney function, sore throat, menstrual irregularities, diseases associated with childbirth, fever, headache pain, and chills as well as symptoms and/or syndromes associated with these conditions.

In addition, the subject invention provides isolated cimiracemate A that can be used as an anti-inflammatory agent.

In a further embodiment, the subject invention makes it possible to distinguish various species of the *Cimicifuga* genus. In accord with the subject invention, the extracts of the various *Cimicifuga* species create individual chemical profiles for cimiracemate A bioactivity.

In one aspect, cimiracemate A can be used according to the subject invention as a chemical marker to standardize commercially available *C. racemosa* products. The use of cimiracemate A as a chemical marker to standardize *C. racemosa* products can be, for example, based on the bioactivity of cimiracemate A as an anti-inflammatory agent.

Advantageously, using the improved extraction procedure of the subject invention it is possible to distinguish different species of *cimicifuga* and to standardize extracts using cimiracemate A as the chemical marker for the potential bioactive use of these herbs or related products as alternative therapeutics or dietary supplements.

DETAILED DESCRIPTION

Figure 1:
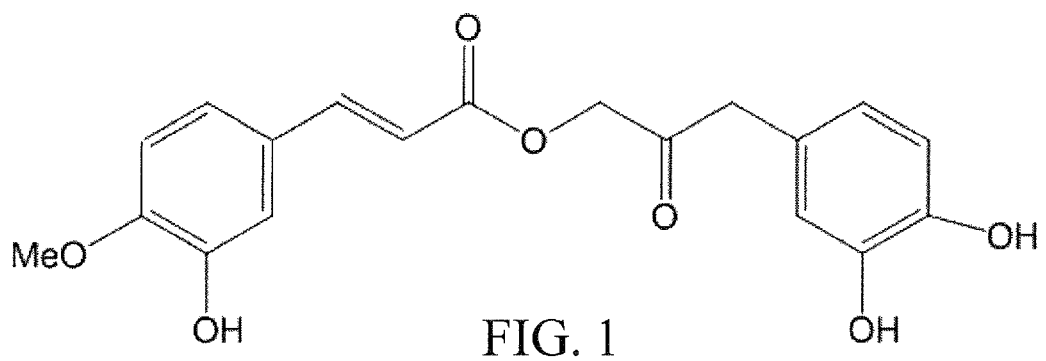
FIG. 1 is a chemical structure of cimiracemate A.

The subject invention provides materials and methods for isolating and extracting cimiracemate A from various species of *Cimicifuga*. In accordance with the subject invention, the isolated cimiracemate A can be used as a therapeutic composition or dietary supplement. In addition, the isolated cimiracemate A can be used as a bioactive chemical marker and standard for various species of *Cimicifuga*.

In a preferred embodiment the subject invention provides a method for purifying cimiracemate A, comprising the steps of:
 a) providing a sufficient quantity of raw material of a *Cimicifuga* species;
 b) grinding the raw material into a powder;
 c) mixing the powder with an aqueous solvent; and
 d) isolating cimiracemate A.

In specific embodiments, the *Cimicifuga* species is selected from *Cimicifuga racemosa, Cimicifuga foetida*, and/or *Cimicifuga heracleifolia*. In a preferred embodiment, the *Cimicifuga* species is Cimicifuga racemosa.

In a further preferred embodiment, the extraction procedure of the subject invention utilizes water, optionally with ethanol, as the solvent. The solvent preferably comprises less than 20% ethanol, more preferably there can be less than 15% ethanol, and even less than 10%, or even less than 5%.

In a preferred embodiment, the subject invention utilizes a ratio of *Cimicifuga racemosa* to water of between 1:5 and 1:20, and preferably about 1:15. In addition, it is preferred that the extraction procedure is carried out at room temperature. This temperature may be, for example, from 20° C. to 28° C. or from 22° C. to 26° C. In a specific embodiment the extraction procedure is carried out at about 25° C.

Advantageously, the subject invention provides higher and more consistent yields of isolated cimiracemate A from

*Cimicifuga* species. The subject invention also provides a more rapid and convenient method of cimiracemate A isolation.

The subject invention provides isolated cimiracemate A for treatment of for example, malaise, malaria, rheumatism, abnormal kidney function, sore throat, menstrual irregularities, diseases associated with childbirth, fever, headache pain, and chills.

In addition, the subject invention provides isolated cimiracemate A that can be used as an anti-inflammatory agent.

The subject invention further provides isolated cimiracemate A that can be used to suppress LPS-induced INFα in human macrophages, inhibit LPS-induced MAP kinase activities, or act as a reactive oxygen species scavenger.

The term "subject," as used herein, describes an organism, including mammals such as primates, to which treatment with the compositions according to the present invention can be provided. Mammalian species that can benefit from the disclosed methods of treatment include, but are not limited to, apes, chimpanzees, orangutans, humans, monkeys; and domesticated animals such as dogs, cats, horses, cattle, pigs, sheep, goats, chickens, mice, rats, guinea pigs, and hamsters.

In a further embodiment, the subject invention makes it possible to distinguish various species of the Cimicifuga genus. In accord with the subject invention, the extracts of the various *Cimicifuga* species create individual chemical profiles for cimiracemate A bioactivity following HPLC.

In one aspect, the isolated cimiracemate A of the subject invention can be used as a chemical marker to standardize commercially available *C. racemosa* products. The use of the isolated cimiracemate A as a chemical marker to standardize commercially available *C. racemosa* products can be, for example, based on the bioactivity of cimiracemate A as an anti-inflammatory agent.

Cimiracemate A has been identified in the dried rhizomes and roots of black cohosh. This compound suppresses the ITS-induced effects including specific kinase phosphorylation, transcription factor activation and TNF-α production in primary human macrophages (U.S. Patent Application No. 61/143,925, filed Jan. 12, 2009; which is incorporated herein by reference in its entirety).

Sample extraction is the crucial first step for extracting maximal amounts of desired chemical components from herbal materials. During the past few years, some modern techniques including the headspace analysis, supercritical and subcritical-fluid extraction, microwave-assisted extraction and pressurized liquid extraction have been used for quantitative preparation in the analysis of medicinal plants (Huie, 2002). Although these methods have significant advantages over conventional methods by reducing organic solvent consumption, eliminating sample clean-up and concentration steps, and improving the extraction efficiency of the herbs, they have important limitations. For example, headspace analysis and supercritical and subcritical-fluid extraction only target the essential oils from herbs, whereas pressurized liquid extractions are performed at elevated temperatures that may lead to thermal degradation. Thus, it is desirable to develop an improved extraction protocol for scaling-up the production of specific compounds from the herbs.

Advantageously, the methods of the subject invention provide high and consistent yields of cimiracemate A extracted from black cohosh. An additional advantage of the methods of the subject invention is that they are rapid and convenient in sample preparation for pharmaceutical uses.

The extraction conditions for cimiracemate A have been improved according to the subject invention by changing the extraction parameters including temperature, extraction solvent, extraction time and solvent volume. HPLC conditions have also been identified that increase the percentage of cimiracemate A obtained from the extracts.

Furthermore, by using the extraction procedures and HPLC conditions as set forth herein, it is possible to establish standards for characterizing herbal products with specific bioactivities.

In addition, cimiracemate A can be used according to the subject invention to identify the members of the *Cimicifuga* genus, for example: *C. racemosa, C. dahurica* (Turcz.) Maxim., *C. foetida* L., and *C. heracleifolia* Kom. Cimiracemate A can also be used to standardize extracts of *Cimicifuga* species for use as anti-inflammatory agents for the treatment of inflammatory-associated diseases. Cimiracemate A can also be used, according to the subject invention, to distinguish species based on the chemical profile of each sample based on, for example, the ratio of cimiracemate A to other compounds in the sample.

Solvent Selectin

Polar, non-toxic solvents, including water and ethanol (and mixtures thereof), were used to extract cimiracemate A from *C. racemosa*. This solvent system is suitable in extracting different polarities of the active constituents as well as acceptable for human consumption. Among the solvents used, water and 20%, or less, ethanol yielded the highest amount of cimiracemate A.

Extraction Temperature

Selection of extraction temperature is also crucial for extracting a higher amount of cimiracemate A from *C. racemosa* according to the subject invention. An increase in temperature had been reported to significantly increase diffusivities by breaking the solute-matrix interaction bonds and to increase the solute volatility (Loncin & Merson 1979). However, n accordance with the current invention, it was determined that the extraction yield of cimiracemate A decreased upon increasing temperature beyond room temperature. This indicated that mobilization of cimiracemate A from the herbs may occur at room temperature (e.g. 25° C.) followed by their possible loss due to decomposition at higher temperatures. Thus, in accordance with the subject invention, room temperature is the preferred extraction temperature for extracting cimiracemate A from *C. racemosa*.

Sonication Treatment

Figure 4:
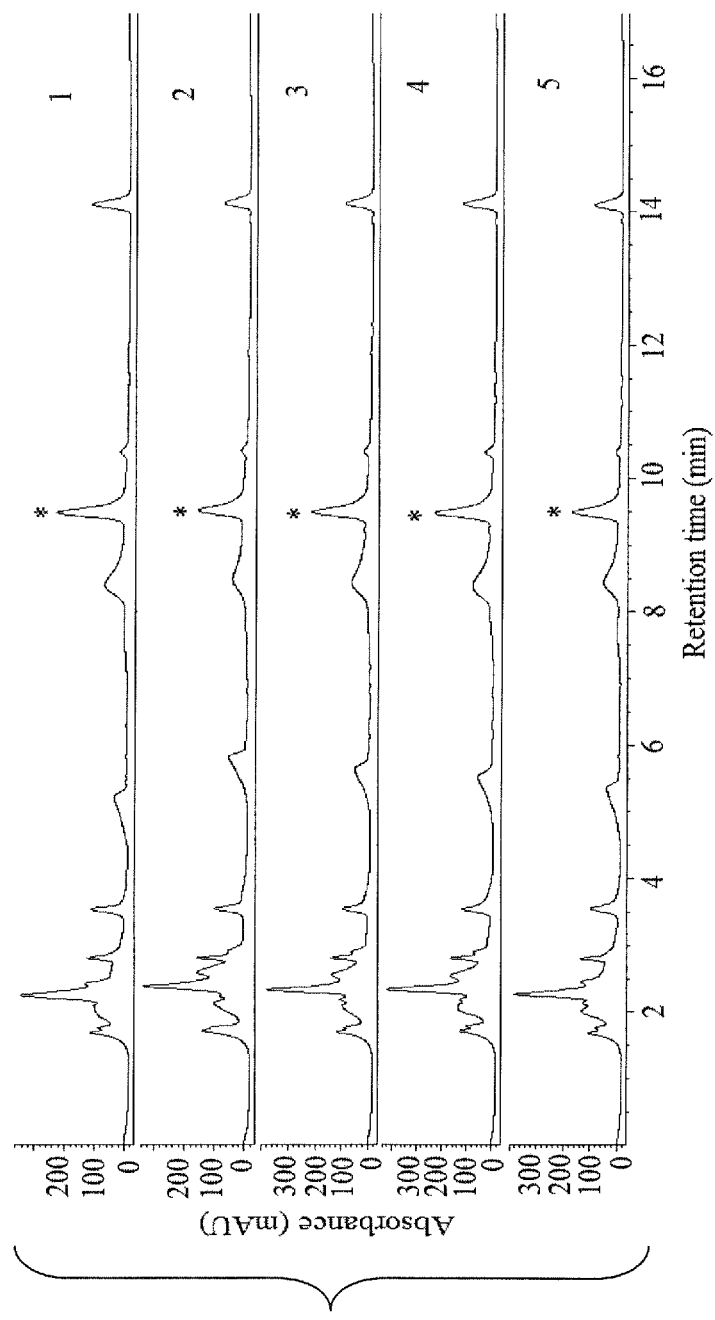
FIG. 4 shows chromatograms of the roots of *C. racemosa* extracted with milli-Q by sonication for (1) 0 min, (2) 5 min, (3) 10 min, (4) 20 min and (5) 30 min. * denotes the presence of cimiracemate A in the samples of *C. racemosa* under different extraction conditions. The chromatograms were obtained by injecting the samples to a reversed-phase high-performance liquid chromatography (Lichrospher 100 RP C18 EC 5μ, 250×4.6 mm ID) using gradient elution from 15% $CH_3CN$ to 100% $CH_3CN$ at a flow rate of 1 ml $min^{-1}$ and the detection wavelength was at 210 nm.
Figure 8:
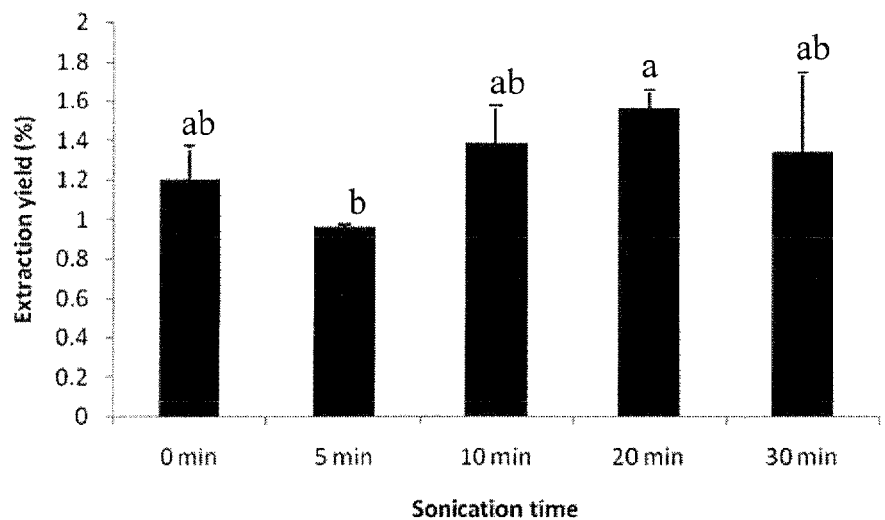
FIG. 8 shows the effect of extraction time on the extraction yield of cimiracemate A (n=3). Experimental conditions: The herb (2.0 g) was extracted with Milli-Q water at room temperature. Different letters above the bars indicate significant differences according to Tukey's test (p<0.05, one-way ANOVA).

Sonication is another method that can, in some cases, improve the efficiency and shorten the extraction time for extracting compounds from dry material of herbs. The underlying mechanism of enhancement is the intensification of mass transfer and easier access of the solvent to the dry material of herbs (Vinatoru, 2001; Shotipruk et al., 2001). In analytical situations, sonication is an expeditious, inexpensive and efficient alternative to conventional extraction techniques and, in some cases, even to supercritical fluid and microwave-assisted extraction (Luque-García et al., 2003). However, in accordance with the current invention, it was found that sonication did not improve the extraction yield of cimiracemate A, when compared to the use of maceration conditions (FIGS. 4 and 8).

The results revealed that cimiracemate A may be leached out from the herbal materials to water easily and did not require any energy. Thus, the extraction of cimiracemate A from *C. racemosa* can utilize cold macerations.

Experimental Materials and Methods

Instruments

An Agilent 1200 series high performance liquid chromatography-photo-diode array (HPLC-DAD) (Palo Alto, Calif., USA) system was used. It was equipped with a G1367c autosampler, a vacuum degasser, a binary pump, a DAD detector and a LC workstation. An ultrasonic bath (J.P. Selecta, Spain) was used for extracting the compounds from the herbs.

Solvents

Deionized water was obtained from a Milli-Q water system (Millipore, Bedford, Mass., USA) for extracting samples and preparing the mobile phase. Ethanol (EtOH, Merck, Germany) of analytical grade was used for the preparation of standard and/or sample solutions. Acetonitrile (ACN, Tedia, USA) of HPLC grade was used for preparation of the mobile phase.

Plant Materials

The raw material of Cimicifuga racemosa was purchased from the Monterey Bay Spice Company (Santa Cruz, USA) in May 2008. The material was grinded into powder form using a grinder (IKA, Germany). The powder was then kept in a desiccator and used in all experiments.

Identification of Preferred Extraction Conditions

Effect of Hydroalcoholic Solvent Ratio

C. racemosa (2 g) was extracted with 10 ml of 0%, 20%, 40%, 60%, 80%, and 100% (v/v) EtOH in water. Extractions were done by sonication for 30 minutes at room temperature. There were three replicates for each solvent. The extraction process was repeated and the experiments were performed three times. The extracts were centrifuged at 4000 rpm for 5 min and then filtered through a filter paper (No 1, Advantec, Japan). The resulting filtrate was evaporated and freeze-dried in order to obtain the dry weight of the extracts.

Effect of Extraction Temperature

Three extraction temperatures (room temperature, 50° C. and 100° C.) were used to study the extraction yield of cimiracemate A. Dried powder of C. racemosa (2.0 g) was sonicated with 10 ml Milli-Q water at each extraction temperatures for 30 min. There were three replicates for each temperature, and the extraction process was repeated three times. The extracts were centrifuged at 4000 rpm for 5 minutes and then filtered through a filter paper as above. The resulting filtrate was then freeze-dried in order to obtain the dry weight of the extracts.

Effect of Sonication Time

C. racemosa (2.0 g) was extracted with 10 ml Milli-Q water at room temperature. Extractions were done by maceration and/or sonication for 5, 10, 20 and 30 minutes. There were three replicates for each extraction time and the extraction process was repeated three times. The extracts were centrifuged at 4000 rpm for 5 minutes and then filtered through a filter paper as above. The resulting filtrate was evaporated and freeze-dried in order to obtain the dry weight of the extracts.

Effect of Solvent-to-Herb Ratio

C. racemosa (2.0 g) was extracted with milli-Q at ratio of 1:5, 1:10, 1:15 and 1:20 (w/v) at room temperature with continuous sonication for 30 minutes. There were three replicates for each extraction volume and the extraction process was repeated three times. The extracts were centrifuged at 4000 rpm for 5 minutes and then filtered through a filter paper as above. The resulting filtrate was evaporated and freeze-dried in order to obtain the dry weight of the extracts.

Quantification Analysis

The dry extracts were dissolved in methanol (MeOH) (25 mg/ml) prior to be determined by HPLC using a reversed phase Lichrospher 100 $C_{18}$ (250×4.6 mm i.d., 5 μm) column (Alltech, USA). Separation was performed by linear gradient elution using ACN (25-90% in 15 minutes) and Milli-Q water (75-10% in 15 minutes). The flowing rate was 1.0 ml/min. The detection wavelength and the column temperature were set at 210 nm and 23° C., respectively. The injection volume was 5 μl. This running condition was optimized to give the best separation of cimiracemate A from the other eluent peaks.

Extraction of C. dahurica (Turcz.) Maxim., C. foetida L., and C. heracleifolia Kom.

Three counterparts of C. racemosa: C. dahurica (Turcz.) Maxim., C. foetida L., and C. heracleifolia Kom. were provided by Purapharm International (H.K.) Ltd. Each herb (2.0 g) was extracted with 40 ml Milli-Q water under sonication (30 minutes) at room temperature. The extraction process was repeated three times and three replicates for each herb were done. The aqueous extracts were freeze-dried and then dissolved in MeOH to obtain the final concentration of 25 mg/ml. The fingerprints of the herbs as well as the percentage yield of cimiracemate A were determined using HPLC-PDA as described above.

Statistical Analysis

Data were analyzed using the SPSS statistical package. The differences of extraction yield of cimiracemate A among the extraction conditions were checked for normality using Shapiro-Wilk's test and for homogeneity of variance using Cochran's C-test. They were then compared using one-way ANOVA followed by Tukey's test. In all cases, the threshold for significance was 5%.

Following are examples that illustrate procedures for practicing the subject invention. These examples are provided for the purpose of illustration only and should not be construed as limiting.

EXAMPLE 1

Optimization of Cimiracemate a Isolation and Extraction

Optimization of HPLC Conditions

Using a bioassay-guided fractionation and identification scheme, cimiracemate A (FIG. 1) with anti-inflammatory activity was isolated from the aqueous extract of C. racemosa. In order to quantify cimiracemate A from each extract, a calibration curve ranged from 0.15625 to 1.25 μg/μl was obtained (y=9197.4x−12.457, $R^2$=0.9993).

Optimization of Extraction Conditions

Effect of Hydroalcoholic Solvent Ratio

Figure 2:
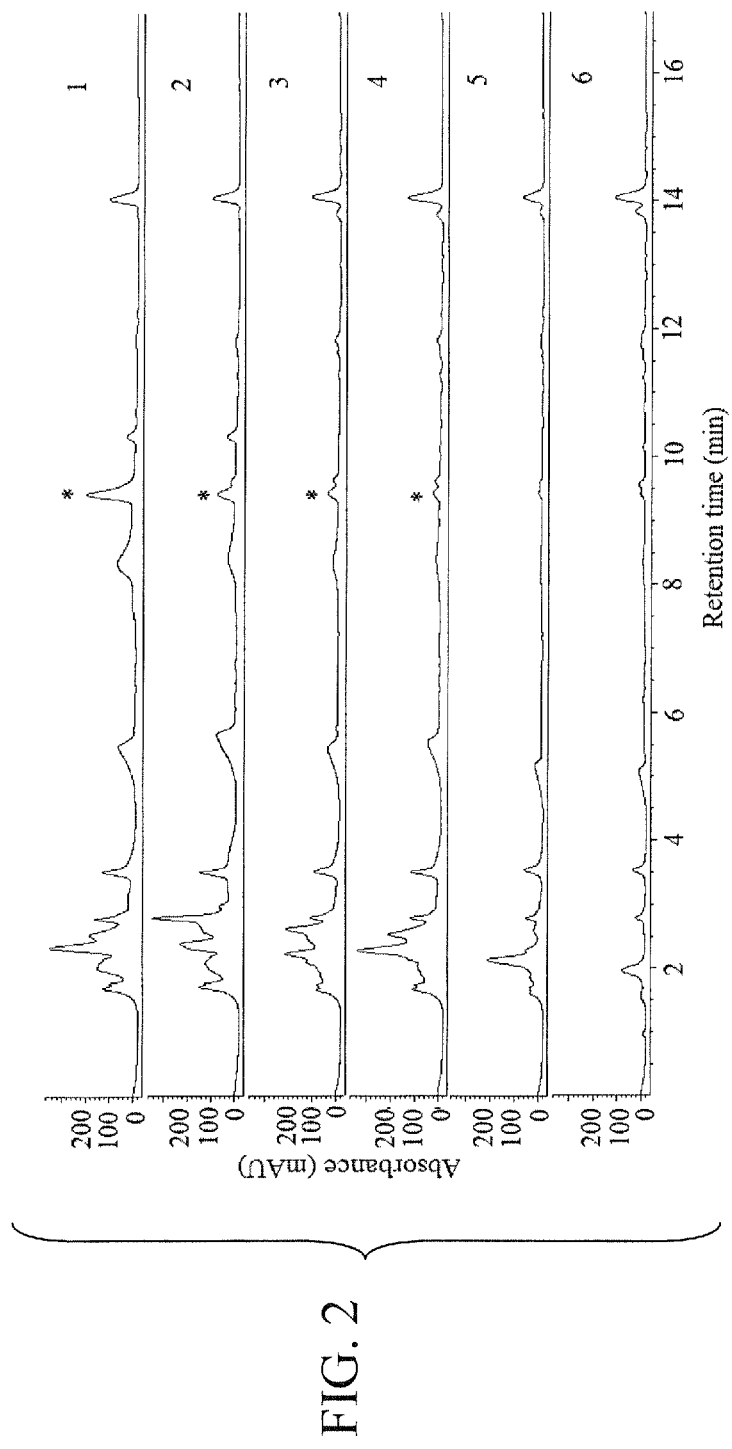
FIG. 2 shows chromatograms of the roots of C racemosa extracted with Milli-Q-ethanol at ratio of (1) 100:0, (2) 80:20, (3) 60:40, (4) 40:60, (5) 20:80 and (6) 0:100. * denotes the presence of cimiracemate A in the samples of *C. racemosa* under different extraction conditions. The chromatograms were obtained by injecting the samples to a reversed-phase high-performance liquid chromatography (Lichrospher 100 RP C18 EC 5μ, 250×4.6 mm ID) using gradient elution from 15% $CH_3CN$ to 100% $CH_3CN$ at a flow rate of 1 ml $min^{-1}$ and the detection wavelength was at 210 nm.
Figure 6:
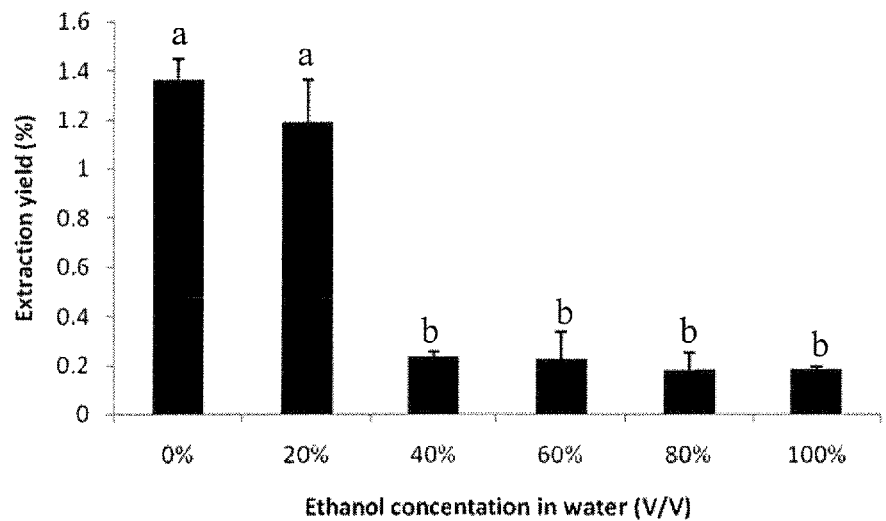
FIG. 6 shows the effect of extraction solvent on the extraction yield of cimiracemate A (n=3). Experimental condition: The herb (2.0 g) was extracted by sonication for 30 min at room temperature and the extraction was repeated three times. Different letters above the bars indicate significant differences according to Tukey's test (p<0.05, one-way ANOVA).

The percentage yields of cimiracemate A in C. racemosa in relation to the ethanol content in the extraction solvent are shown in FIGS. 2 and 6. As shown in FIG. 2, the peak of cimiracemate A (denoted as *) was the highest at 0% ethanol (i.e. 100% water) and it reduced substantially with the increase of ethanol content. The extraction yield of cimiracemate A decreased from 1.36 to 0.19% when the ethanol content increased from 0 to 100% (FIG. 6). The results indicated that the ethanol content affects the extraction of cimiracemate A from C. racemosa, with the extraction efficiency decreased with the increase of ethanol content in the extraction solvent. Therefore, water was used as the extraction solvent for the further investigations.

Effect of Extraction Temperature

Figure 3:
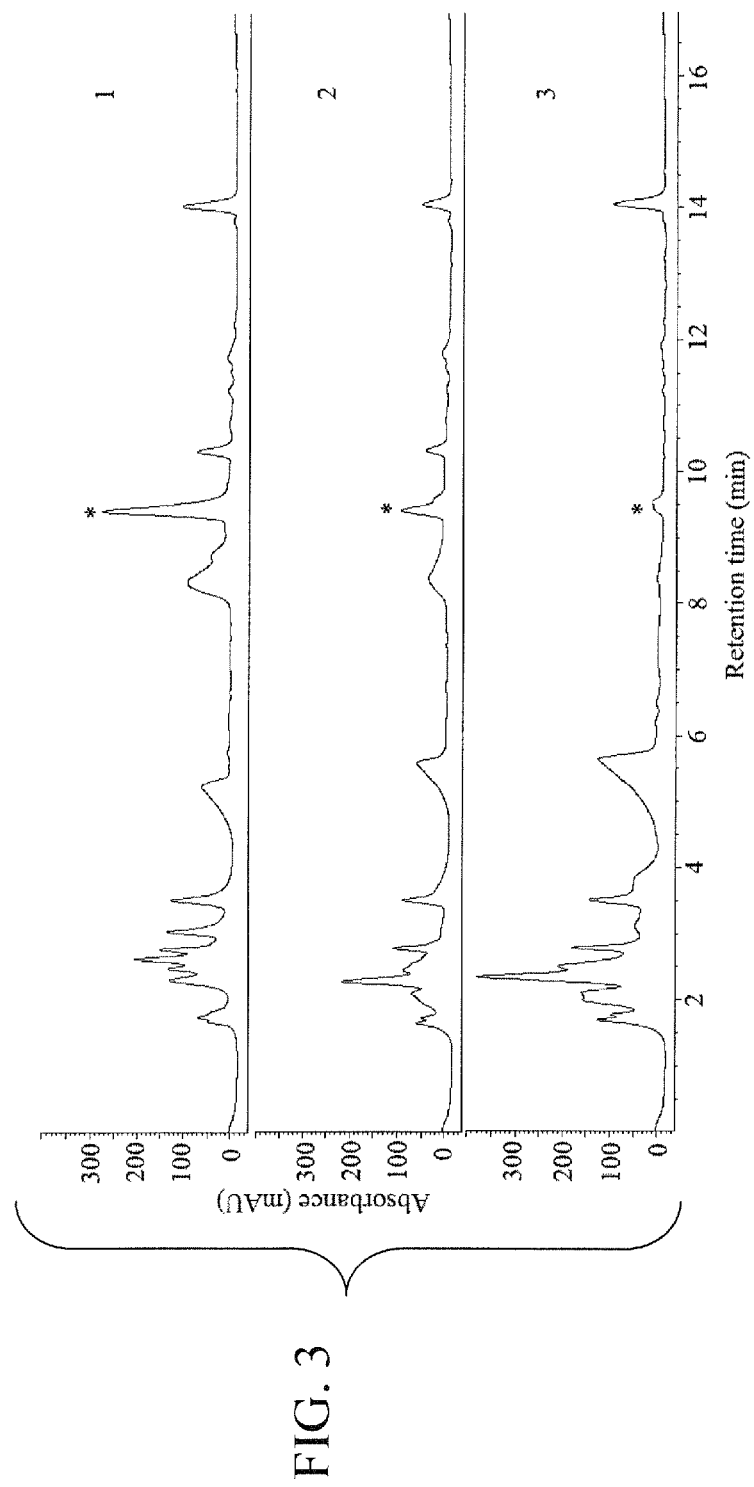
FIG. 3 shows chromatograms of the extracts obtained by extracting the roots of *C. racemosa* with milli-Q at (1) room temperature, (2) 50° C. and (3) 100° C. * denotes the presence of cimiracemate A from the samples of *C. racemosa* under different extraction conditions. The chromatograms were obtained by injecting the samples to a reversed-phase high-performance liquid chromatography (Lichrospher 100 RP C18 EC 5μ, 250×4.6 mm ID) using gradient elution from 15% $CH_3CN$ to 100% $CH_3CN$ at a flow rate of 1 ml $min^{-1}$ and the detection wavelength was at 210 nm.
Figure 7:
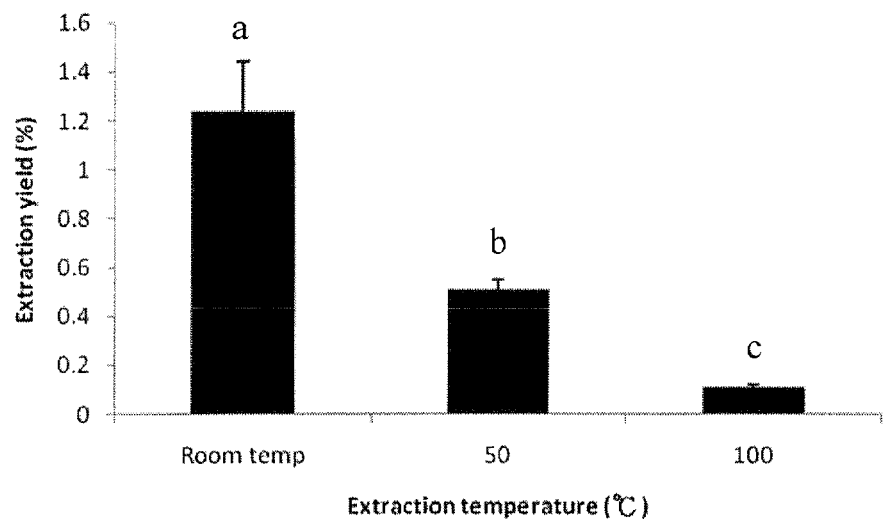
FIG. 7 shows the effect of temperature on the extraction yield of cimiracemate A (n=3). Experimental conditions: the amount of herb 2.0 g; the extraction time 30 min; the extraction solvent Milli-Q water (10 ml). The extraction was repeated three times. Different letters above the bars indicate significant differences according to Tukey's test (p<0.05, one-way ANOVA).

In order to investigate how temperature affects the extraction yield of cimiracemate A, C. racemosa were extracted under three different thermal conditions: room temperature, 50 and 100° C. In FIG. 3, the chromatograms of the extracts obtained from optimized HPLC condition were shown. The peak of cimiracemate A (denoted as *) was the highest at room temperature and reduced substantially from room temperature to 50° C. and then to 100° C. (FIG. 3). In addition, the extraction yields of cimiracemate A at room temperature, 50 and 100° C. were 1.24, 0.51 and 0.11%, respectively (FIG. 7). The results indicated that temperature affected the extraction yield of cimiracemate A significantly (Tukey's test, $p<0.05$) and the extraction efficiency of cimiracemate A decreased substantially with increases in temperature. Therefore, room temperature was chosen for further investigations.

Effect of Sonication Time

The percentage yields of cimiracemate A extracted from *C. racemosa* undergoing different sonication time are presented in FIGS. 4 and 8. In FIG. 4, the peaks of cimiracemate A appeared in all the extracts with similar intensity. The percentage yield of cimiracemate A was determined to be 1.20, 0.96, 1.39, 1.56, and 1.34% with sonication time for 0, 5, 10, 20, and 30 min (FIG. 8), respectively. Our results indicated that sonication did not significantly increase the extraction yield of cimiracemate A (Tukey's test, $p>0.05$).

Effect of Solvent-to-Herb Ratio

Figure 5:
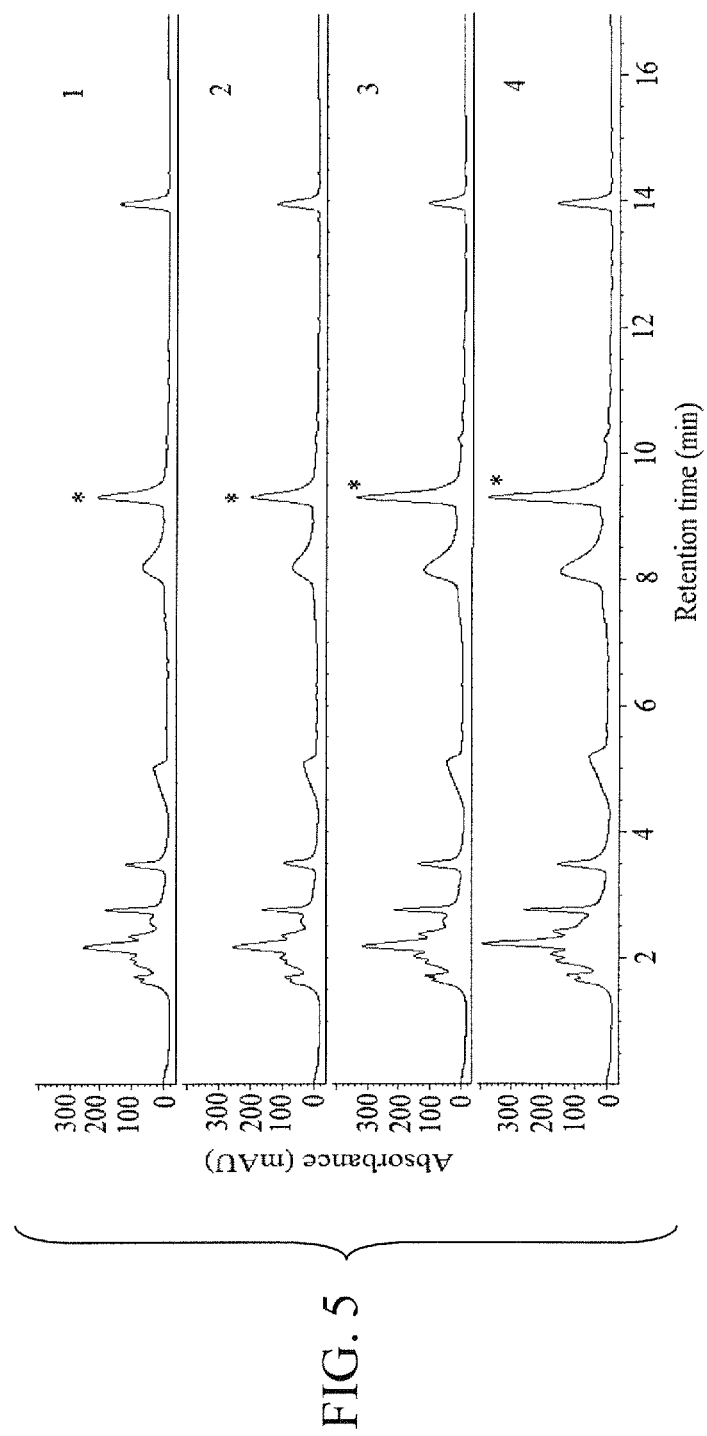
FIG. 5 shows chromatograms of the roots of *C. racemosa* extracted with milli-Q at ratio of (1) 1:5 (w/v), (2) 1:10 (w/v), (3) 1:15 (w/v) and (4) 1:20 (w/v). * denotes the presence of cimiracemate A in the samples of *C. racemosa* under different extraction conditions. The chromatograms were obtained by injecting the samples to a reversed-phase high-performance liquid chromatography (Lichrospher 100 RP C18 EC 5μ, 250×4.6 mm ID) using gradient elution from 15% $CH_3CN$ to 100% $CH_3CN$ at a flow rate of 1 ml $min^{-1}$ and the detection wavelength was at 210 nm.
Figure 9:
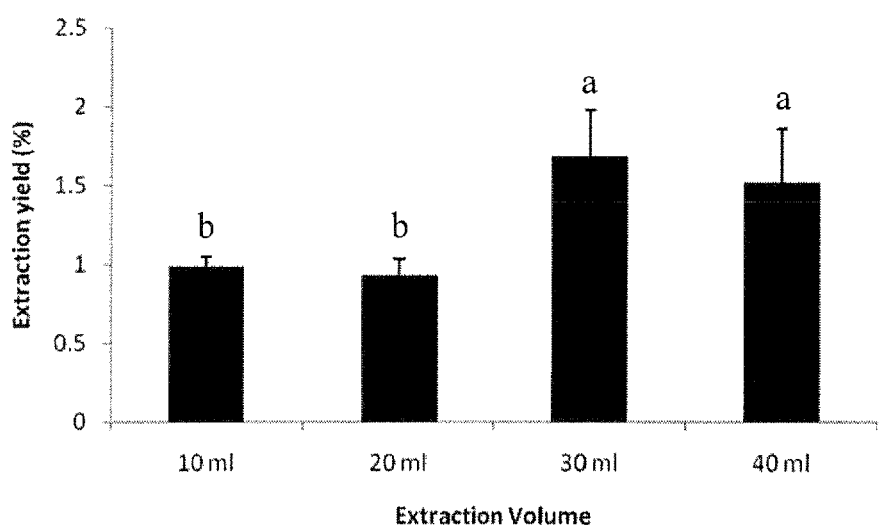
FIG. 9 shows the effect of solvent volume on the extraction yield of cimiracemate A (n=3). Experimental conditions: The herb (2.0 g) was extracted with Milli-Q water for 30 min at room temperature. The extraction was repeated three times. Different letters above the bars indicate significant differences according to Tukey's test (p<0.05, one-way ANOVA).

The effect of solvent volume on extraction efficiency of cimiracemate A from *C. racemosa* was determined by extracting the herbs with at a ratio of 1:5, 1:10, 1:15 and 1:20 (w/v). The results showed that the peak intensity of cimiracemate A obtained from 1:15 and 1:20 (w/v) was higher than the other two ratios (FIG. 5). In FIG. 9, the percentage yield of cimiracemate A was determined to be 0.98, 0.93, 1.68, and 1.52% at a ratio of 1:5, 1:10, 1:15 and 1:20 (w/v) of water, respectively. The results revealed that the ratio of *C. racemosa* to water should be higher than 1:15 (w/v) in order to obtain a higher extraction yield of cimiracemate A.

EXAMPLE 2

Cimiracemate a Isolation and Fingerprinting for Determining the Identity and Bioactivity of Cimicifuga Species Determination of Cimiracemate a from *C. dahurica, C. foetida*, and *C. heracleifolia*

Figure 10A:
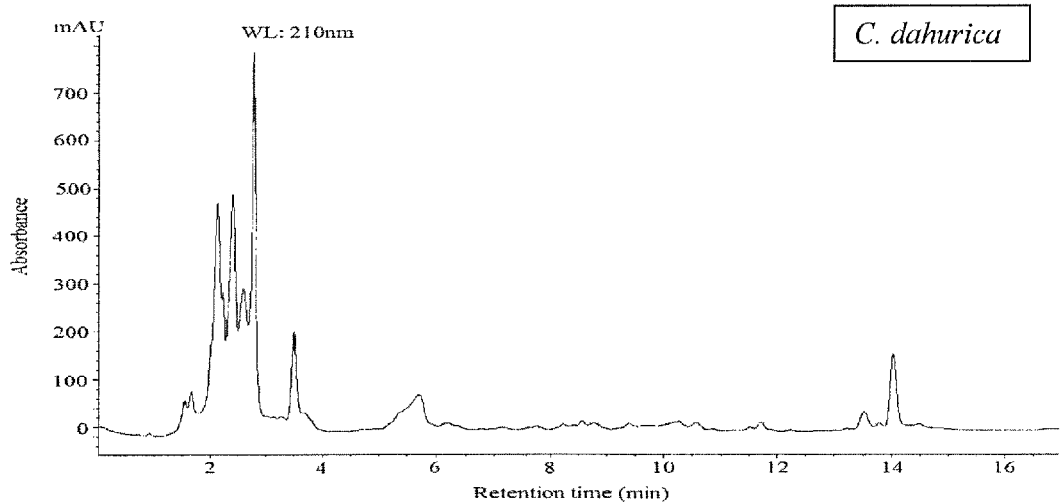
FIG. 10A-C shows the chromatographic fingerprints of *C. dahurica, C. foetida*, and *C. heracleifolia*. * denotes the presence of cimiracemate A in the samples The chromatograms were obtained by injecting the samples to a reversed-phase high-performance liquid chromatography (Lichrospher 100 RP C18 EC 5μ, 250×4.6 mm ID) using gradient elution from 15% $CH_3CN$ to 100% $CH_3CN$ at a flow rate of 1 ml $min^{-1}$ and the detection wavelength was at 210 nm.
Figure 10B:
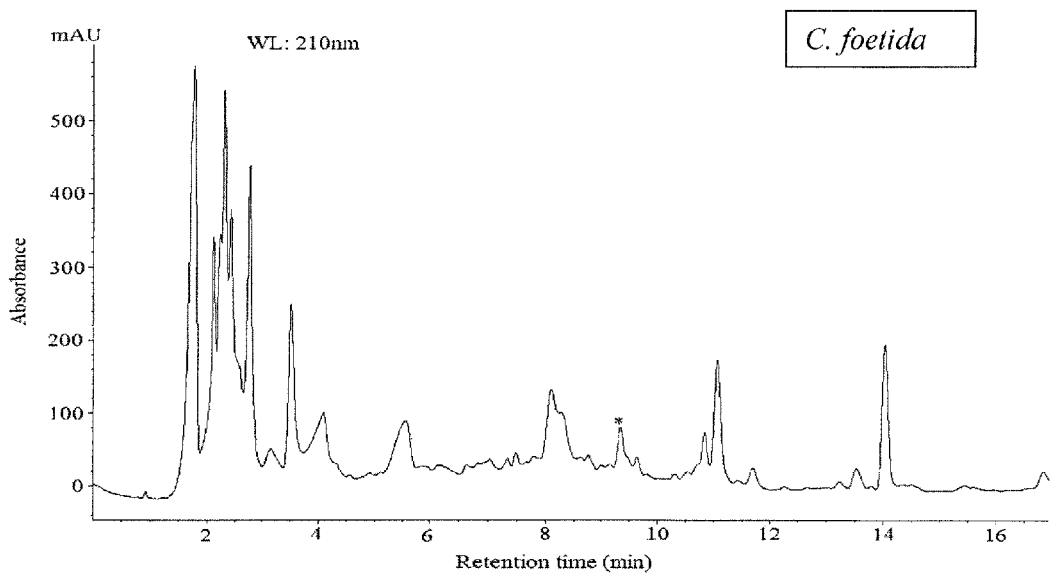
Figure 10C:
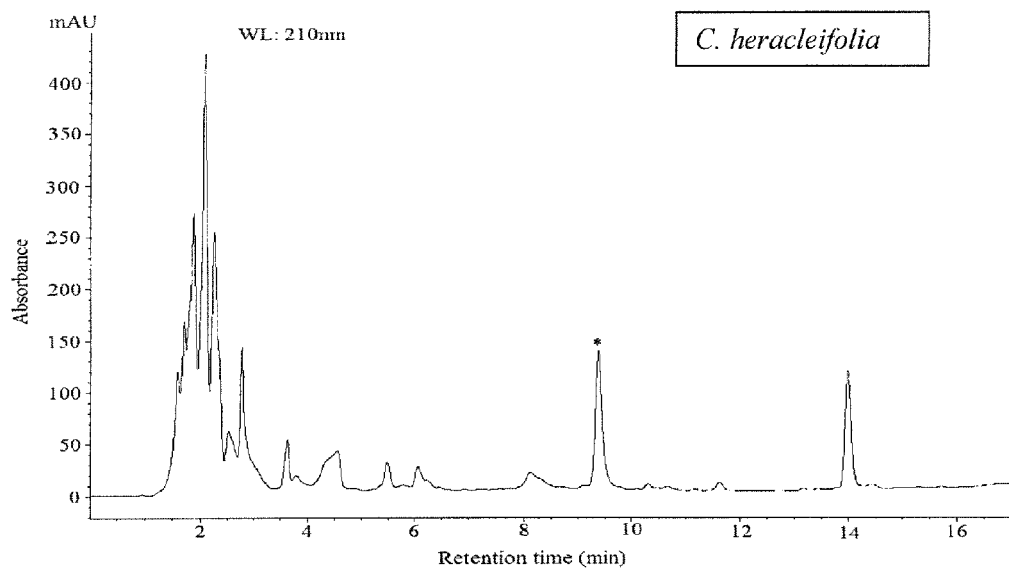

The reference fingerprints of *C. dahurica, C. foetida*, and *C. heracleifolia* were determined by extracting the herbs under the same optimized extraction condition and followed by running the same HPLC setting to that of black cohosh. The results showed that *C. dahurica* did not contain cimiracemate A whereas *C. foetida*, and *C. heracleifolia* contained different levels of cimiracemate A as shown in FIG. 10. In general, using the same optimized extraction and HPLC conditions, it is easy to identify the compound in raw herbs of *C. racemosa* as well as its counterparts, namely *C. foetide* and *C. heracleifolia*.

EXAMPLE 3

Therapeutic Uses of Cimiracemate A

The compounds of the subject invention can be used to treat inflammation associated with infection, including, but not limited to, infections by viruses, bacteria, fungi, yeast, and other microbes. Additionally, the compounds of the subject invention can be used to treat inflammation mediated by a variety of proinflammatory factors including, but not limited to, tumor necrosis factor, interferons, interleukins, leukotrienes, and environmental toxins.

The compounds and pharmaceutical compositions of the present invention can be used in the treatment, or amelioration, of inflammatory symptoms in any disease, condition or disorder where immune and/or inflammation suppression is beneficial. Inflammatory diseases, conditions or disorders in which the compounds and compositions of the present invention can be used to inhibit unwanted immune reactions and inflammation include, but are not limited to, arthritis, including but not limited to rheumatoid arthritis, and other diseases, conditions or disorders of the joints or musculoskeletal system in which immune and/or inflammation suppression is beneficial.

Moreover, the compounds and compositions are also useful to treat or ameliorate inflammation associated with atherosclerosis; arteriosclerosis; atherosclerotic heart disease; reperfusion injury; cardiac arrest; myocardial infarction; vascular inflammatory disorders including cerebro-vascular disease (stroke); respiratory distress syndrome and other cardiopulmonary diseases, conditions or disorders where immune and/or inflammation suppression, such as graft-versus-host disease and allergic conditions, would be beneficial.

In addition, the compounds and compositions are also useful to treat or ameliorate inflammation associated with peptic ulcer; ulcerative colitis, Chron's Disease, irritable bowel syndrome, other inflammatory bowel conditions, and other diseases, conditions or disorders of the gastrointestinal tract where immune inflammation suppression would be beneficial; hepatic fibrosis; liver cirrhosis and other hepatic diseases, conditions or disorders where immune and/or inflammation suppression would be beneficial; thyroiditis and other glandular diseases, conditions or disorders where immune and/or inflammation suppression would be beneficial; glomerulonephritis and other renal and urologic diseases, conditions or disorders where immune and/or inflammation suppression would be beneficial.

In addition, the compounds and compositions are also useful to treat or ameliorate inflammation associated with post-traumatic inflammation; septic shock; infectious diseases where immune and/or inflammation suppression would be beneficial; inflammatory complications and side effects of surgery where immune and/or inflammation suppression would be beneficial; bone marrow transplantation and other transplantation complications and/or side effects where immune and/or inflammation suppression would be beneficial; inflammatory and/or immune complications and side effects of gene therapy, e.g., due to infection with a viral carrier; and inflammation associated with acquired immune deficiency syndrome (AIDS).

Further, the compounds and compositions are also useful to inhibit macrophage or T cell associated aspects of an immune response that are not associated with inflammation. The compounds and compositions are able to inhibit macrophage or T cell activities including, but not limited to, macrophage antigen-presenting activity, macrophage cytokine production, T cell cytokine production, T cell adhesion activity, T cell proliferation, etc. Thus, the peptides, peptide derivatives and compositions are useful to suppress or inhibit a humoral and/or cellular immune response.

The compounds and compositions are also useful to treat or ameliorate monocyte and leukocyte proliferative diseases, e.g., leukemia, by reducing the amount of monocytes and lymphocytes.

The compounds and pharmaceutical compositions of the invention are further useful for the prevention and/or treatment of graft rejection in cases of transplantation of natural or artificial cells, tissue and organs, such as cornea, bone marrow, organs, lenses, pacemakers, natural and artificial skin tissue, and the like.

The compounds and compositions are also useful to treat or ameliorate inflammation associated with hypersensitivity; allergic reactions; asthma; systemic lupus erythematosus; collagen diseases and other autoimmune diseases, conditions or disorders in which immune and/or inflammation suppression is beneficial.

The compounds and compositions are also useful to treat or ameliorate inflammation associated with otitis and other otorhinolaryngological diseases, conditions or disorders where immune and/or inflammation suppression would be beneficial; dermatitis and other dermal diseases, conditions or disorders where immune and/or inflammation suppression would be beneficial; periodontal diseases and other dental diseases, conditions or disorders where immune and/or inflammation suppression would be beneficial.

In addition, the compounds and compositions are also useful to treat or ameliorate inflammation associated with posterior uveitis; intermediate uveitis; anterior uveitis; conjunctivitis; chorioretinitis; uveoretinitis; optic neuritis; intraocular inflammation, such as retinitis and cystoid macular edema; sympathetic ophthalmia; scleritis; retinitis pigmentosa; immune and inflammatory components of degenerative fondus disease; inflammatory components of ocular trauma; ocular inflammation caused by infection; proliferative vitreoretinopathies; acute ischemic optic neuropathy; excessive scarring, for example, following glaucoma filtration operation; immune and/or inflammation reaction against ocular implants and other immune and inflammatory-related ophthalmic diseases, conditions or disorders where immune and/or inflammation suppression would be beneficial.

Moreover, the compounds and compositions are also useful to treat or ameliorate inflammation associated with autoimmune diseases and conditions or disorders where, both in the central nervous system (CNS) and in any other organ, immune and/or inflammation suppression would be beneficial; Parkinson's disease; complications and/or side effects from treatment of Parkinson's disease; AIDS-related dementia complex (HIV-related encephalopathy); Devic's disease; Sydenham chorea; Alzheimer's disease and other degenerative diseases, conditions or disorders of the central nervous system where immune and/or inflammation suppression would be beneficial; inflammatory components of strokes; post-polio syndrome; immune and inflammatory components of psychiatric disorders; myelitis; encephalitis; subacute sclerosing panencephalitis; encephalomyelitis; acute neuropathy; subacute neuropathy; chronic neuropathy; Guillaim-Barre syndrome; Sydenham chorea; myasthenia gravis; pseudotumor cerebri; Down's Syndrome; Huntington's disease; amyotrophic lateral sclerosis; inflammatory components of central nervous system (CNS) compression or CNS trauma or cerebrovascular accidents (stroke) or infections or hypoxia-ischemia of the CNS; inflammatory components of muscular atrophies and dystrophies; and immune and inflammatory related diseases, conditions or disorders of the central and peripheral nervous systems where immune and/or inflammation suppression would be beneficial.

In yet another embodiment, the compounds and compositions of the invention are useful to restore immune privilege at an immune privileged site which has lost its immune privilege such as brain, eye and testis.

EXAMPLE 4

Formulations

In one embodiment, the subject invention provides isolated compounds. As used herein, "isolated" refers to compounds that have been removed from any environment in which they may exist in nature. For example, isolated cimiracemate A would not refer to the cimiracemate A compound as it exists in *Cimicifuga racemosa*. In preferred embodiments, the compounds of the subject invention are at least 75% pure, preferably at least 90% pure, more preferably are more than 95% pure, and most preferably are more than 99% pure (substantially pure).

The present invention also provides for therapeutic or pharmaceutical compositions comprising a compound of the invention in a form that can be combined with a pharmaceutically acceptable carrier. In this context, the compound may be, for example, isolated or substantially pure. The term "carrier" refers to a diluent, adjuvant, excipient, or vehicle with which the compound is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers, particularly for injectable solutions. Particularly preferred pharmaceutical carriers for treatment of or amelioration of inflammation in the central nervous system are carriers that can penetrate the blood/brain barrier. As used herein carriers do not include the natural plant material as it exists in nature.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The therapeutic composition, if desired, can also contain minor amounts of wetting or emulsifying agents, or pH buffering agents. These compositions can take the form of solutions, suspensions, emulsion, tablets, capsules, powders, sustained-release formulations and the like. The composition can be formulated with traditional binders and carriers such as triglycerides. Examples of suitable pharmaceutical carriers are described in "Remington's Pharmaceutical Sciences" by E. W. Martin. Such compositions contain a therapeutically effective amount of the therapeutic composition, together with a suitable amount of carrier so as to provide the form for proper administration to the patient. The formulation should suit the mode of administration.

In one embodiment, the composition is formulated in accordance with routine procedures as a pharmaceutical composition adapted for local injection administration to human beings. Typically, compositions for local injection administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile water for injection or saline can be provided so that the ingredients may be mixed prior to administration.

The therapeutic or pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The present invention also provides for the modification of the compound such that it is more stable once administered to a subject, i.e., once administered it has a longer time period of effectiveness as compared to the unmodified compound. Such modifications are well known to those of skill in the art, e.g., polyethylene glycol derivatization (PEGylation), microencapsulation, etc. In specific examples, an active compound of the invention can be coupled to large or small molecular-weight PEGs by using a linker. Previously-known examples of such constructs include PEG-irinotecan and PEG-docetaxel.

The amount of the therapeutic or pharmaceutical composition of the invention which is effective in the treatment of a particular disease, condition or disorder will depend on the nature of the disease, condition or disorder and can be determined by standard clinical techniques. In general, the dosage ranges from about 0.001 mg/kg to about 2 mg/kg. In addition, in vitro assays may optionally be employed to help identify optimal dosage ranges. The precise dose to be employed in the formulation will also depend on the route of administration, and the seriousness of the disease, condition or disorder, and should be decided according to the judgment of the practitioner and each patient's circumstances. Effective doses may be extrapolated from dose-response curves derived from in vitro or animal model test systems. For example, in order to obtain an effective mg/kg dose for humans based on data generated from rat studies, the effective mg/kg dosage in rats is divided by six.

The invention also provides a pharmaceutical pack or kit comprising one or more containers filled with one or more of the ingredients, e.g., compound, carrier, of the pharmaceutical compositions of the invention.

The compounds of the subject invention can also be formulated consistent with traditional Chinese medicine practices. The composition and dosage of the formulation that are effective in the treatment of a particular disease, condition or disorder will depend on the nature of the disease, condition or disorder by standard clinical techniques.

The traditional Chinese medicine in prescription amounts can be readily made into any form of drug, suitable for administering to humans or animals. Suitable forms include, for example, tinctures, decoctions, and dry extracts. These can be taken orally, applied through venous injection or mucous membranes. The active ingredient can also be formulated into capsules, powder, pallets, pastille, suppositories, oral solutions, pasteurized gastroenteric suspension injections, small or large amounts of injection including preparations for intravenous administration, frozen power injections, pasteurized powder injections and the like. All of the above-mentioned methods are known to people skilled in the art, described in books and commonly used by practitioners of herbal medicine.

A tincture is prepared by suspending herbs in a solution of alcohol, such as, for example, wine or liquor. After a period of suspension, the liquid (the alcohol solution) may been administered for example, two or three times a day, one teaspoon each time.

A decoction is a common form of herbal preparation. It is traditionally prepared in a clay pot, but can also be prepared in glass, enamel or stainless steel containers. The formulation can be soaked for a period of time in water and then brought to a boil and simmered until the amount of water is reduced by, for example, half.

An extract is a concentrated preparation of the essential constituents of a medicinal herb. Typically, the essential constituents are extracted from the herbs by suspending the herbs in an appropriate choice of solvent, typically, water, ethanol/water mixture, methanol, butanol, iso-butanol, acetone, hexane, petroleum ether or other organic solvents. The extracting process may be further facilitated by means of maceration, percolation, repercolation, counter-current extraction, turbo-extraction, or by carbon-dioxide hypercritical (temperature/pressure) extraction. After filtration to rid of herb debris, the extracting solution may be further evaporated and thus concentrated to yield a soft extract (extractum spissum) and/or eventually a dried extract, extracum siccum, by means of spray drying, vacuum oven drying, fluid-bed drying or freeze-drying. The soft extract or dried extract may be further dissolved in a suitable liquid to a desired concentration for administering or processed into a form such as pills, capsules, injections, etc.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

References

1. Aggarwal S, Takada Y, Singh S, Myers J N, Aggarwal B. Inhibition of growth and survival of human head and neck squamous cell carcinoma cells by curcumin via modulation of nuclear factor-kappaB signaling. *Int J Cancer* 2004, 111: 679-92.
2. Blumenthal M, Goldberg A, Brinckmann J (eds.): Herbal Medicine: Expanded Commission E Monographs. Newton, Mass.: Integrative Medicine Communications, 2000, pp 22-27.
3. Burdette J E, Chen S N, Lu Z Z, Xu H, White B E, Fabricant D S, Liu J, Fong H S, Farnsworth N R, Constantinou A I, Van Breemen R V, Pezutto J M, Bolton J L. Black cohosh (*Cimicifuga racemosa* L.) protects against menadione-induced DNAdamage through scavenging of reactive oxygen species: bioassay-directed isolation and characterization of active principles. *J Agric Food Chem* 2002, 50: 7022-7028.
4. Cacace J E, Mazza G. Optimization of extraction of anthocyanins from black currants with aqueous ethanol. *J Food Sci* 2003, 68: 240-248.
5. Chen H, Fabricant D S, Pauli G F, Fong H H S, Farnsworth NR. Synthesis of Cimiracemate B, a phenylpropanoid found in Cimicifuga Racemosa. *Nat Prod Res* 2005, 19: 287-290.
6. Chen H. Zhang Z S, Zhang Y L, Zhou D Y. Curcumin inhibits cell proliferation by interfering with the cell cycle and inducing apoptosis in colon carcinoma cells. *Anticancer Res* 1999, 19: 3675-3680.
7. Chen S N, Fabricanta D S, Lua Z Z, Zhanga H, Fong H H S, and Farnswortha N R. Cimiracemates A-D, phenylpropanoid esters from the rhizomes of *Cimicifuga racemosa*. *Phytochemistry* 2002, 61: 409-413.
8. Foster S. Black cohosh: Cimicifuga racemosa. A literature review. *HerbalGram* 1999, 45: 35-49.
9. He K, Pauli G F, Zheng B, Wang H, Bai N, Peng T, Roller M, Zheng Q. *Cimicifuga* species identification by high performance liquid chromatography-photodiode array/mass spectrometric/evaporative light scattering detection for quality control of black cohosh products. *J Chromatogr A*, 2006, 1112: 241-254.

10. Huic C W. A review of modern sample-preparation techniques for the extraction and analysis of medicinal plants. *Anal Bioanal Chem* 2002, 373: 23-30.
11. Itokawa H, Aiyama R, Ikuta A. A pungent principle from *Alpinia oxyphylla Phytochemistry* 1982, 21: 241-243.
12. Iversen C K. Black currant nectar: Effect of processing and storage on anthocyanin and ascorbic acid. *J Food Sci* 1999, 64: 37-41.
13. Kennelly K J, Baggett S, Nuntanakorn P, Ososki A L, Mori S A, Duke J, Coleton M, Kronenberg F. Analysis of thirteen populations of black cohosh for formononetin. *Phytomedicine* 2002, 9: 461-467.
14. Kim C D, Lee W K, Lee M H, Cho H S, Lee Y K, Roh S S. Inhibition of mast cell-dependent allergy reaction by extract of black cohosh (*cimicifuga racemosa*). *Immunopharmacol Immunotoxicol* 2004, 26: 299-308.
15. Kim S J, Kim M S. Inhibitory effects of *Cimicifugae rhizoma* extracts on histamine, bradykinin and COX-2 mediated inflammatory actions. *Phytother Res* 2000, 14: 596-600.
16. Kusano A, Seyama Y, Nagai M, Shibano M, Kusano G Effects of Fukinolic Acid and Cimicifugic Acids from *Cimicifuga* Species on Collagenolytic Activity. *Biol Pharm Bull* 2001, 24: 1198-1201.
17. Li W, Chen S, Fabricant D, Angerhofer C K, Fong H H S, Farnsworth N R, Fitzloff J F. High-performance liquid chromatographic analysis of Black Cohosh (*Cimicifuga racemosa*) constituents with in-line evaporative light scattering and photodiode array detection. *Analytica Chimica Acta* 2002, 471:61-75.
18. Loncin M, Merson R L. Food engineering: principles and selected applications, Academic Press 1979, New York, USA
19. Luque-Garci'a J L, Luque de Castro M D. Ultrasound: a powerful tool for leaching. *Trends in Anal Chem* 2003, 22: 41-47.
20. Ohishi K, Aiyama R, Hatano H, Yoshida Y, Wada Y Yokoi W, Sawada H, Watanabe T, Yokokura T. Structure-Activity Relationships of N-(3,5-Dimethoxy-4-n-octyloxycinnamoyl)-N-(3,4-dimethylphenyl)piperazine and Analogues as Inhibitors of Acyl-CoA: Cholesterol O-Acyltransferase. *Chem Pharm Bull* 2001, 49: 830-839.
21. Pepping J P D. Black cohosh: *Cimicifuga racemosa. Am J of Health-Sys Pharm* 1999, 56: 1400-1402.
22. Roughley P J, Whiting D A. Experiments in the biosynthesis of curcumin. *J Chem Soc Perkin Trans* 1973, 1: 2379-2388.
23. Shotipruk A, Kaufman P B, Wang H Y. Feasibility study of repeated harvesting of menthol from biologically viable *Mentha xpiperata* using ultrasonic extraction, *Biotechnol Prog* 2001, 17: 924-928.
24. Skrede Wrolstad R E, Durst R W. Changes in anthocyanins and polyphenolics during juice processing of highbush blueberries (*Vaccinium corymbosum* L.), *J Food Sci* 2000, 65: 357-364.
25. Vinatoru M. An overview of the ultrasonically assisted extraction of bioactive principles from herbs. *Ultrason Sonochem* 2001, 8: 303-313.
26. Yang C L H, Chik, S C C, Li J C B, Cheung B K W, Lau A S Y. Identification of the bioactive constituent and its mechanisms of action in mediating the anti-inflammatory effects of Black Cohosh and related *Cimicifuga* species on human primary blood macrophages, submitted to *J Med Chem*, jm-2009-006164 (incorporated herein in its entirety by reference).

We claim:

1. A method for isolating cimiracemate A from a *Cimicifuga* species, comprising the steps of:
   a) providing a sufficient quantity of raw material of a *Cimicifuga* species;
   b) mixing the raw material of a *Cimicifuga* species with a solvent at a temperature of 20° C. to 28° C. to obtain a solvent extract comprising cimiracemate A, wherein the solvent is water-ethanol comprising ethanol at a concentration of less than 20%; and
   c) isolating cimiracemate A from the solvent extract to yield a liquid or dried composition comprising cimiracemate A.

2. The method of claim 1, wherein cimiracemate A is isolated from the solvent extract using high-performance liquid chromatography (HPLC).

3. The method of claim 2, wherein cimiracemate A is eluted using HPLC from the solvent extract at UV absorbance of about 210 nm.

4. The method of claim 3, wherein cimiracemate A is eluted using HPLC from the solvent extract at about 23° C.

5. The method of claim 1, wherein the raw material of a *Cimicifuga* species is ground into powder.

6. The method of claim 1, wherein the *Cimicifuga* species is selected from the group consisting of *Cimicifuga racemosa*, *Cimicifuga foetida*, and *Cimicifuga heracleifolia*.

7. The method of claim 6, wherein the *Cimicifuga species* is *Cimicifuga racemosa*.

8. The method of claim 1 claim 1, wherein the *Cimicifuga* species is mixed with water-ethanol at a ratio of about 1:15 to about 1:20 (w/v).

9. A method for isolating cimiracemate A from a *Cimicifuga* species, consisting of the steps of:
   a) providing a sufficient quantity of raw material of a *Cimicifuga* species;
   b) mixing the raw material of a *Cimicifuga* species with a solvent at a temperature of 20° C. to 28° C. to obtain a solvent extract comprising cimiracemate A, wherein the solvent is water or water-ethanol comprising ethanol at a concentration of less than 20%; and
   c) isolating cimiracemate A from the solvent extract to yield a liquid composition comprising cimiracemate A.

10. The method of claim 9, wherein the solvent is water.

11. The method of claim 10, wherein the *Cimicifuga* species is mixed with water at a ratio of about 1:15 to about 1:20 (w/v).

12. A method for preparing a composition comprising the isolated cimiracemate A from claim 1, further comprising formulating the isolated cimiracemate A into a composition selected from the group consisting of tablets, capsules, powders, pastilles, suppositories, oral solutions, suspensions, and injectable compositions.

13. The method of claim 12, comprising formulating the isolated cimiracemate A into a composition selected from the group consisting of tablets, capsules, powder, and pastilles.

14. A method for isolating cimiracemate A from a *Cimicifuga* species, comprising the steps of:
   a) providing a sufficient quantity of raw material of a *Cimicifuga* species;
   b) mixing the raw material of a *Cimicifuga* species with water as the solvent at a temperature of 20° C. to 28° C. to obtain a water extract comprising cimiracemate A; and
   c) isolating cimiracemate A from the water extract to yield a liquid or dried composition comprising cimiracemate A.

15. The method of claim 14, wherein the raw material of a *Cimicifuga* species is ground into powder.

16. The method of claim 14, wherein the *Cimicifuga* species is selected from the group consisting of *Cimicifuga racemosa*, *Cimicifuga foetida*, and *Cimicifuga heracleifolia*.

17. The method of claim 16, wherein the *Cimicifuga* species is *Cimicifuga racemosa*.

18. The method of claim 14, wherein the *Cimicifuga* species is mixed with water at a ratio of about 1:15 to about 1:20 (w/v).

19. The method of claim 17, wherein *Cimicifuga racemosa* is mixed with water at a ratio of about 1:15 (w/v).

20. A method for preparing a composition comprising the isolated cimiracemate A from claim 14, further comprising formulating the isolated cimiracemate A into a composition selected from the group consisting of tablets, capsules, powders, pastilles, suppositories, oral solutions, suspensions, and injectable compositions.

21. The method of claim 20, comprising formulating the isolated cimiracemate A into a composition selected from the group consisting of tablets, capsules, powder, and pastilles.

* * * * *

UNITED STATES PATENT AND TRADEMARK OFFICE
CERTIFICATE OF CORRECTION

PATENT NO.        : 8,633,332 B2                                           Page 1 of 1
APPLICATION NO.   : 13/379008
DATED             : January 21, 2014
INVENTOR(S)       : Yang et al.

It is certified that error appears in the above-identified patent and that said Letters Patent is hereby corrected as shown below:

In the Specification

Column 1,
Line 8, "PCT/AB2010/001772," should read --PCT/IB2010/001772,--.

Column 5,
Line 13, "INFα in" should read --TNFα in--.

Column 5,
Line 38, "ITS-induced" should read --LPS-induced--.

Column 8,
Line 38, "Cimiracemate a" should read --Cimiracemate A--.

Column 9,
Line 38, "Cimiracemate a" should read --Cimiracemate A--.

Column 9,
Line 42, "a from C" should read --A from C--.

Column 15,
Line 1, "Huic CW." Should read --Huie CW.--.

Signed and Sealed this
Twenty-ninth Day of July, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,633,332 B2
APPLICATION NO.  : 13/379008
DATED            : January 21, 2014
INVENTOR(S)      : Yang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 154 days.

Signed and Sealed this

Twenty-second Day of September, 2015

Michelle K. Lee
*Director of the United States Patent and Trademark Office*